(12) United States Patent
Bödewadt et al.

(10) Patent No.: US 9,788,841 B2
(45) Date of Patent: Oct. 17, 2017

(54) IMPLANTABLE MEDICAL DEVICE WITH LUMEN CONSTRICTION

(71) Applicant: COOK MEDICAL TECHNOLOGIES LLC, Bloomington, IN (US)

(72) Inventors: Tue Thuren Bödewadt, Herfoelge (DK); Christina Rauff Hansen, Koebenhavn (DK); Erik E. Rasmussen, Slagelse (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 208 days.

(21) Appl. No.: 14/749,060

(22) Filed: Jun. 24, 2015

(65) Prior Publication Data

US 2015/0374383 A1   Dec. 31, 2015

(30) Foreign Application Priority Data

Jun. 25, 2014   (GB) .................................. 1411283.3
Mar. 25, 2015   (EP) .................................. 15275087

(51) Int. Cl.
*A61M 29/00*   (2006.01)
*A61B 17/12*   (2006.01)
(Continued)

(52) U.S. Cl.
CPC .. *A61B 17/12145* (2013.01); *A61B 17/12109* (2013.01); *A61B 17/12172* (2013.01);
(Continued)

(58) Field of Classification Search
CPC ........ A61B 17/12022; A61B 17/12172; A61B 17/0057; A61B 17/12109;
(Continued)

(56) References Cited

U.S. PATENT DOCUMENTS 5,108,420 A    4/1992   Marks
5,984,944 A   11/1999   Forber
(Continued)

FOREIGN PATENT DOCUMENTS

DE   19509464 C1   6/1996
DE   19607451 A1   9/1997
(Continued)

OTHER PUBLICATIONS

Extended European Search Report for EP15275087.3-1651, dated Oct. 29, 2015.
(Continued)

*Primary Examiner* — Jonathan Miles
*Assistant Examiner* — Majid Jamialahmadi
(74) *Attorney, Agent, or Firm* — Brinks Gilson & Lione

(57) ABSTRACT

An implantable medical device includes a support structure which is twistable in a longitudinal direction of the device. A sleeve of filter or occluding material is attached to the ends of the structure. The structure in practice twists on itself in the longitudinal direction, causing the sleeve to twist on itself and as a result to close the lumen through the sleeve. The device provides reliable closure and as a result occlusion of a vessel. It is also able to be delivered over a guide wire. In another embodiment, the support structure includes a wire which coils around the sleeve to constrict the sleeve and as a result to close a lumen of the sleeve.

10 Claims, 3 Drawing Sheets

(51) Int. Cl.
    *A61F 2/01*            (2006.01)
    *A61F 2/82*            (2013.01)
    *A61B 17/00*            (2006.01)

(52) U.S. Cl.
    CPC .......... *A61B 17/12177* (2013.01); *A61F 2/01* (2013.01); *A61F 2/013* (2013.01); *A61F 2/82* (2013.01); *A61B 2017/00862* (2013.01); *A61B 2017/00867* (2013.01); *A61B 2017/12054* (2013.01); *A61F 2002/016* (2013.01); *A61F 2210/0014* (2013.01); *A61F 2210/0076* (2013.01); *A61F 2230/001* (2013.01); *A61F 2230/0078* (2013.01); *A61F 2230/0091* (2013.01)

(58) Field of Classification Search
    CPC .... A61B 17/12145; A61B 2017/00862; A61B 2017/12054; A61F 2/01; A61F 2/82; A61F 2/24; A61F 2/2427; A61F 2/88; A61F 2/95; A61F 2/07; A61F 2002/823; A61F 2002/072; A61F 2002/011
    USPC ..... 606/157, 200, 213; 623/1.11, 1.13, 1.15, 623/1.24, 1.26, 1.2
    See application file for complete search history.

(56) References Cited

U.S. PATENT DOCUMENTS

| | | | |
|---|---|---|---|
| 6,117,157 A | 9/2000 | Tekulve | |
| 6,254,633 B1 | 7/2001 | Pinchuk et al. | |
| 8,361,138 B2 | 1/2013 | Adams | |
| 8,372,113 B2 | 2/2013 | Opolski | |
| 8,372,114 B2 | 2/2013 | Hines | |
| 2002/0123759 A1 | 9/2002 | Amplatz | |
| 2002/0156499 A1 | 10/2002 | Konya et al. | |
| 2003/0153935 A1* | 8/2003 | Mialhe | A61B 17/0057 606/157 |
| 2006/0058820 A1 | 3/2006 | Mialhe | |
| 2007/0078504 A1 | 4/2007 | Mialhe | |
| 2007/0239199 A1 | 10/2007 | Jayaraman | |
| 2008/0051830 A1* | 2/2008 | Eidenschink | A61B 17/0057 606/213 |
| 2009/0171386 A1 | 7/2009 | Amplatz et al. | |
| 2009/0177221 A1 | 7/2009 | Kramann | |
| 2009/0187214 A1 | 7/2009 | Amplatz et al. | |
| 2009/0216261 A1 | 8/2009 | Brandeis et al. | |
| 2009/0216263 A1 | 8/2009 | Tekulve | |
| 2010/0163054 A1 | 7/2010 | Breznel et al. | |
| 2011/0319906 A1 | 12/2011 | Rudakov et al. | |
| 2012/0083822 A1 | 4/2012 | Anukhin et al. | |

FOREIGN PATENT DOCUMENTS

| | | |
|---|---|---|
| WO | WO 97/27893 | 8/1997 |
| WO | WO 2008/100382 A2 | 8/2008 |
| WO | WO 2011/154828 A2 | 12/2011 |

OTHER PUBLICATIONS

Examination Report for GB1411283.3, dated May 20, 2016.
Combined Search and Examination Report for GB1411283.3, dated Jan. 15, 2015.
Search Report for GB 1411283.3, dated Sep. 17, 2015.

* cited by examiner

IMPLANTABLE MEDICAL DEVICE WITH LUMEN CONSTRICTION

CROSS-REFERENCE TO RELATED APPLICATIONS

This application claims the benefit of priority under 35 U.S.C. §119(a) to European Patent Application No. EP 15275087.3, filed Mar. 25, 2015, and to Great Britain Patent Application No. GB 1411283.3, filed Jun. 25, 2014, which are hereby incorporated by reference in their entirety.

TECHNICAL FIELD

The present invention relates to an implantable medical device, in the preferred embodiments to an occluder or filter deployable in a vessel or other organ of a patient.

BACKGROUND ART

Many different forms of implantable medical devices are known for treating a wide variety of medical conditions. Examples of such devices include vena cava filters and occlusion devices, which are advantageously implanted into a patient by an endoluminal delivery procedure from a remote access point up to the treatment site. It is important for such devices to be able to be located precisely in the vessel with good patency to the vessel wall, that is to fit closely against the vessel wall so as to minimise, preferably avoid, leakage around the device. It is also important for such devices to be stable over time, particularly to exhibit minimal risk of migration and minimal loss of orientation in the vessel. Such devices should also seek to minimise damage to the vessel wall so as to seek to avoid trauma to the vessel, which can cause stenosis and other adverse effects.

In general terms there are two kinds of occlusion devices. A first kind generates instant occlusion of a vessel by a mechanical closure of the device. The other kind of vascular occlusion device relies upon the generation of a thrombus at the occlusion device to close off any residual passage through the device. This latter form of vascular occlusion device typically slows the flow of blood in the vessel, which causes clotting at the location of the device and as a consequence the formation of an occluding barrier. Instant mechanical occluders, while being preferable for many medical indications, can involve less than optimal delivery procedures, particularly given that many conventional occluders of this nature are not suitable for delivery over a guide wire. Some devices which are modified to be able to be delivered over a guide wire require additional steps during the deployment process, additional components and/or have relatively poorer delivery characteristics such as poor radial compressibility and flexibility when in the delivery configuration. Some occlusion devices also suffer from the risk of recanalization of the vessel over time.

Similar considerations apply to filters and other similar implantable medical devices.

Some examples of implantable medical devices are described in US-2010/0163054, U.S. Pat. No. 6,254,633, US-2006/0058820 and US-2003/0153935.

SUMMARY OF THE INVENTION

The present invention seeks to provide an improved implantable medical device.

According to an aspect of the present invention, there is provided an implantable medical device, including: first and second radially expandable end elements disposed in spaced longitudinal relationship relative to one another, each of the first and second end elements including an interior passage; an intermediate element connected between the first and second end elements, the intermediate element providing a passage constriction; wherein the intermediate element is formed of a sprung member of twisted unbiased configuration which provides said passage constriction, the sprung member being twistable against spring bias in a direction opposite a direction of twist to open the passage constriction; wherein the device is an occlusion or filter device and includes a tube of occluding or filtering material, the tube including first and second ends attached to respective ones of the first and second end elements and extending across the intermediate element.

This structure provides a device which is naturally closed but in which the sprung member can be biased to open a passage through the device. Such passage allows a guide wire to be fed through the device, enabling the device to be deployed over the wire. Once deployed and the biasing force removed, the sprung member will return to its rest configuration, constricting and preferably closing the passage through the device. This is automatic and does not require any additional components or deployment steps. Moreover, the device is able to provide, when configured as an occluder or filter, immediate occlusion or filtering once deployed, that is not dependent upon the creation of a thrombus to close any remaining aperture or passage in the device. As will be apparent below, the preferred embodiments can have a small delivery footprint, that is diameter when radially constrained on an introducer assembly, and can retain flexibility both when deployed and during its endoluminal introduction into a patient. Occlusion or filtering is mechanical and with, in the preferred embodiment, no significant risk of recanalization of the vessel.

Advantageously, the intermediate element provides a through passage within an interior of the device when twisted against the spring bias. Preferably, the through passage is formed by at least one of expansion and rotation of tube member within the intermediate element.

It is preferred that the intermediate element closes an interior passage extending through the device, thereby to provide total immediate occlusion in embodiments where the device is configured as an occluder and similarly complete immediate filtering when configured as a filter.

In some embodiments, the device is an occlusion or filter device and includes a tube of occluding or filtering material attached at ends thereof to respective ones of the first and second end element and extending across the intermediate element.

Advantageously, the end elements may be ring shaped, for example in the form of at least one stent ring. They may for instance each be formed of one or more stent rings of zigzag, sinusoidal or other known structure.

At least the intermediate element may be formed from spring steel or a shape memory material.

It is preferred, though not essential, that the end elements and the intermediate element are formed of the same material.

The end elements and the intermediate element may be integral with one another.

In this aspect, the intermediate element may also have a stent structure, in which the structure is biased to a twisted or otherwise closed form.

According to another aspect of the present invention, there is provided an implantable medical device, including: first and second spaced radially expandable end elements, each of the first and second end elements providing an interior passage; a tubular member disposed in the interior passages through the first and second radially expandable elements and extending between the first and second spaced radially spaced expandable elements, the tubular member having a lumen therewithin; and a wire element attached between the first and second spaced radially expandable elements, the wire being woundable around the tubular member into a coil of a plurality of turns; wherein coiling of the wire element causes radial constriction of the tubular member and thereby of the lumen thereof.

This aspect provides a structure in which the central passage of the device can be closed reliably by multiple turns of the wire. The procedure can be carried out readily by a clinician during the deployment process and does not require voluminous additional components which may contribute to an increase in the size of the device or to a reduction in its radial compressibility which could adversely impact on its endoluminal introduction into the patient.

Preferably, coiling of the wire element causes closure the lumen of the tubular element, that is complete and immediate closure of the passage through the device.

In some embodiments, the device is an occlusion device and the tubular member is formed of occluding material. In other embodiments the device is a filter device and the tubular member is formed of filtering material.

The intermediate element may be formed from a plastically deformable material. In other embodiments at least the intermediate element may be formed from spring steel or from a shape memory material.

Advantageously, the end elements and the intermediate element are formed of the same material. The end elements and the intermediate element may be integral with one another.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Various embodiments of implantable medical device are described below and shown in the accompanying drawings.

It is be understood that the drawings are schematic only and are not intended to show the various components of the device to scale. In many cases, the device has been depicted in enlarged form for the sake of clarity of disclosure. The skilled person will appreciate that the device may be configured to a variety of different shapes and sizes in order to correspond to the vessel or other organ in which the device is to be implanted.

The implantable medical devices covered by the scope of this disclosure are intended to be delivered into a patient by means of an endoluminal procedure from a remote percutaneous entry point. A typical procedure may involve the well-known Seldinger technique. The various devices taught herein are ideally suited to be delivered over the wire, that is over a guide wire which is initially inserted into the patient's vasculature. Deployment over a guide wire provides significant advantages, as is known in the art.

The specific embodiments described below are directed to an occlusion device which is designed to occlude a body vessel. It is to be understood, however, that the device could equally be configured as a filter device, in which case the occluding element of the device could be replaced by a filter element, for instance a mesh sleeve or the like. In this regard, there is no general difference in the structures of the two different types of device, save for the occlusion/filtering element. Moreover, it is also envisaged that the teachings herein can be used for other forms of implantable medical device, including for instance flow diverters and so on.

Figure 1:
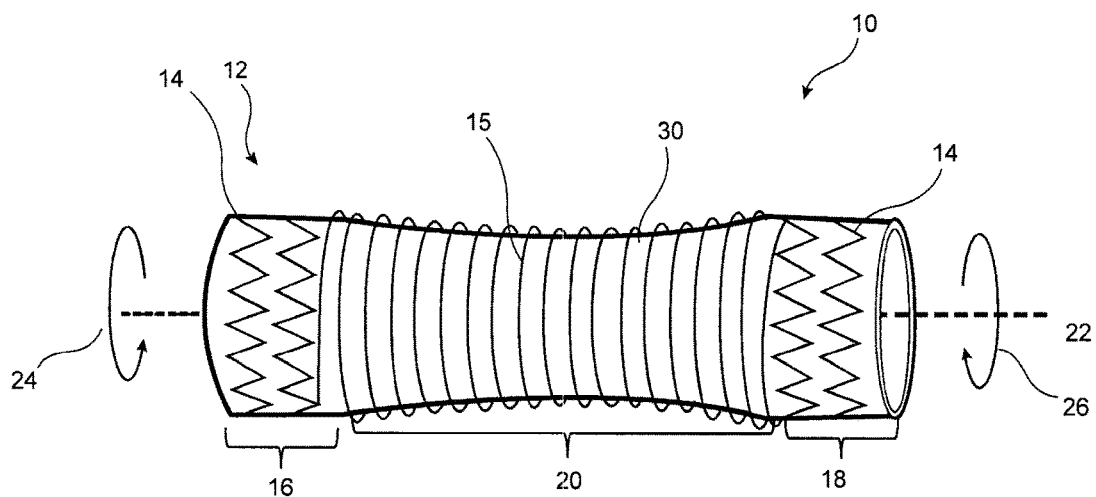
FIG. 1 is a schematic diagram of an embodiment of implantable medical device.

Referring first to FIG. 1, this shows an example of implantable medical device 10 for implantation into the vessel of a patient. The device 10 includes a frame structure 12 which in this example comprises a plurality of stent rings 14 at either end of the device and a sprung element 15 between the stent rings 14. The support structure 12 has a generally tubular form when the device is in what could be considered a twisted biased, or open, condition as shown.

More specifically, the support structure 12 is formed of first and second end elements 16, 18 which in this embodiment are made of radially expandable stents 14 each having an annular and generally cylindrical configuration. The end elements 16, 18 could each be formed of a single stent ring or from a plurality of serially interconnected stent rings. The end elements 16, 18 have a configuration that they will typically expand radially outwardly from their radially compressed delivery configuration.

The structure 12 also includes an intermediate element or section 20 which extends between the first and second end elements 16, 18. The intermediate section 20 is also expandable, in this embodiment to a generally tubular form, although this need not necessarily be into a cylindrical shape as depicted in the drawings as in other embodiments the intermediate section 20 could have a waist, for instance. The intermediate section 20 is, in this embodiment, formed by a sprung member, for instance a wire coiled in a plurality of turns and able to twist around the longitudinal axis 22 of the device 10 as shown by the arrows 24, 26. The coil 15 can be twisted to the configuration shown in FIG. 1 by applying a twisting biasing force at the ends 16, 18. Such a twisting force will load the coil 15 into the biased configuration, that is will act against the spring force generated by the structure of the coil 15. Once the twisting force is removed from the end members 16, 18 the coil 15 will rotate back in the opposite direction to its unbiased configuration.

The coil 15 may be made of a shape memory material such as nickel titanium alloy (Nitinol) or a spring material such as spring steel. When made of a shape memory material, the device 10 can be constructed such that the coil 15 has a shape memory which is twisted relative to its delivery configuration. In use, the coil 15 is twisted when in the austenite phase, during which the material exhibits plastic deformation properties (in other words is super elastic). Once the device 10 passes through its transition temperature, typically around body temperature, the shape memory material will transition through to its martensitic phase, and then cause the coil 15 to revert to its memory shape, that is to its tight coiled configuration.

Disposed within the support structure 12, in this embodiment, is a sleeve or tubular element 30, made of occluding material when the device is to be an occluder. Suitable materials will be well known to the person skilled in the art and can include, for example, materials typically used for grafts. Examples include but are not limited to ultrahigh molecular weight polyethylene such as Dyneema™ and expanded polytetrafluoroethylene.

The sleeve 30 is disposed within the lumen of the support structure 12 and is fixed at either end, specifically to the first and second end elements 16, 18. The sleeve 30 is not attached to the coil 15, for reasons which will become apparent below.

Figure 2:
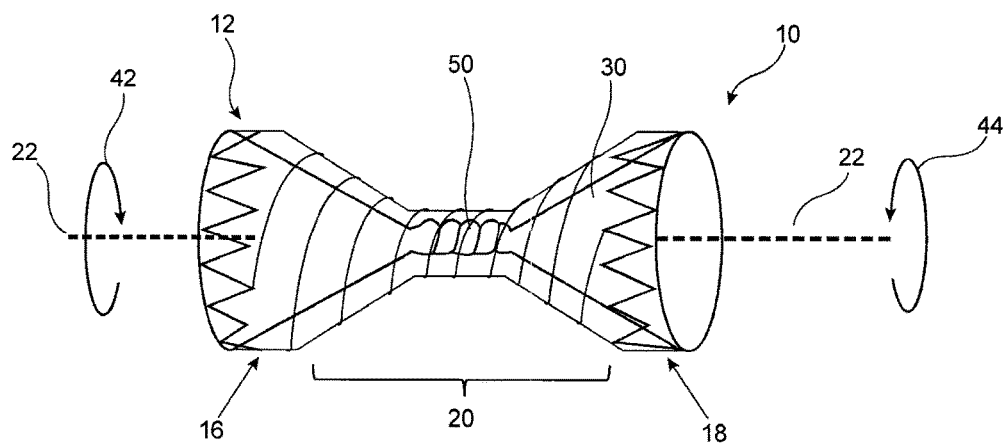
FIG. 2 is a schematic diagram of the implantable medical device of FIG. 1 in a deployed configuration.

Referring now to FIG. 2, this shows in schematic form the device 10 in its fully deployed configuration, that is once the structure 10 has been allowed to recover its untwisted configuration, specifically by allowing one or both of the end elements 16, 18 of the device to rotate in the direction counter to the direction of twist, indicated by the arrows 42, 44. In the embodiment shown in FIG. 2, the support structure 12, that is the coil spring 15 in the example of FIG. 1, constricts within the area of the intermediate section 20 when it twists back again to its unbiased configuration.

As can be seen in FIG. 2, the rotation of the end elements 16, 18 in the opposite direction will cause the sleeve or tubular element 30 to twist on itself as its ends, attached to the end elements 16, 18, are forced to rotate with the end elements 16, 18. This twisting and the fact that the tube or sleeve 30 is connected only at its ends to the support structure 12 causes the sleeve to twist on itself as shown at 50 in FIG. 3. This twisting causes a constriction to, and preferably complete closure of, the passage or lumen passing though the device 10.

It is preferred that the device 10 twists by a plurality of turns of the end elements 16, 18 such that the tube or sleeve 30 is also twisted on itself a plurality of times, as depicted in the sketch of FIG. 2. Multiple twisting of the tube or sleeve 30 in this manner ensures the creation of a secure and strong closure to the passage or lumen through the device 10 and effective occlusion of the vessel. In practice, the sleeve 30 could twist by anything from one turn to a multiple of turns. Furthermore, as can be seen in FIG. 2, the constricted part of the sleeve 30 has a certain length, which enhances the occluding function compared to occluders having only a short occluding barrier. A greater number of turns will increase the length of the constriction.

It will be appreciated that in some embodiments the tube or sleeve 30 will reduce in length as it twists from the configuration shown in FIG. 1 to the configuration shown in FIG. 2. This can be accommodated by making the sleeve initially longer than the space within the structure 12. In other embodiments, the tube or sleeve 30 could be made of an elastic material able to stretch and as a result able to retain the same or a similar length as it moves from the cylindrical open configuration of FIG. 1 to the closed twisted configuration of FIG. 2.

Figure 3:
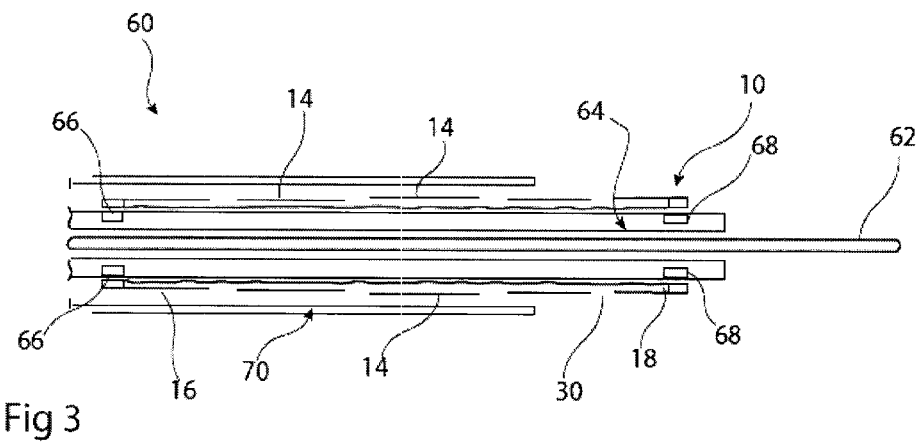
FIG. 3 is a schematic diagram of the distal end of an example of introducer assembly designed to hold a medical device of the types shown in FIGS. 1 and 2 for endoluminal deployment in a patient.

Referring to FIG. 3, this shows an example of an introducer assembly 60 and in particular the distal end thereof, for deploying a medical device 10 of the type shown in FIGS. 1 and 2. It is to be understood that the elements of the introducer assembly shown in FIG. 3 are solely exemplary and also of simplified form, for the sake of clarity of disclosure. The introducer assembly 60 includes a guide wire 62, which can be of conventional type used to guide the elements of the introducer assembly through the patient's vasculature from a remote percutaneous entry point. The assembly 60 also includes a carrier catheter 64 which carries the implantable medical device 10 thereon, suitably restrained at locations 66-68, which may include restraining wires, restraining cups or other elements to hold the proximal distal ends of the device 10 firmly secured to the carrier catheter 64 during storage and the deployment process. The person skilled in the art will readily be able to determine suitable restraining elements 66, 69 as these can be of types conventional in the art.

As will be apparent from FIG. 3, the implantable medical device 10 is retained on the carrier catheter 64 in its twisted and biased configuration as shown in FIG. 1, and thus in a configuration in which the sleeve 30 is substantially open and cylindrical. As is conventional with such introducer assemblies, there may also be provided a sheath 70 which covers the implantable medical device and carrier elements until the device 10 is ready for deployment at the desired treatment site.

Figure 4:
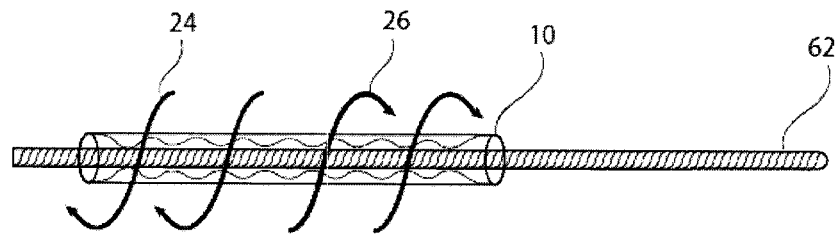
FIG. 4 is a schematic diagram depicting the loading configuration of the device of FIGS. 1 and 2 onto an introducer assembly of the type shown in FIG. 4.

Referring to FIG. 4, this depicts in schematic form how the device 10 is twisted along the longitudinal axis to open the passage or lumen therethrough and so as to fit over a guide wire 62.

The device 10 is deployed by releasing the end element 18 from the carrier catheter 64 and allowing the intermediate section 20, that is the coil 15, to twist back to its non-biased configuration. As will be apparent and as described above, this will happen automatically when the device is made of a spring material such as spring steel or from a shape memory material having passed through its transition point. It is preferred that the deployment of the device, 10 is by release of one of the end elements 16, 18 before the other, such that the device 10 deploys sequentially along its length.

The device shown in FIG. 1 provides automatic closure of the lumen or passage through the device on deployment and therefore immediate mechanical occlusion of the vessel in which the device is fitted. The twisting of the tube or sleeve 30 within the support structure 12 of the device 10, creates a secure closure to the passage or lumen with no realistic risk of recanalization.

Furthermore, the structure of the device 10 is relatively simple, with minimal components, giving the device a small footprint for deployment, that is it enables the device 10 to be radially contracted to a small diameter. The structure is also suitable for devices having a very small deployed diameter, therefore useful in small vessels such as the cerebral vessels. Moreover, the structure is flexible, particularly in the longitudinal direction, by avoiding having to have any components to the device 10 which are rigid or substantially rigid. Having a device which is longitudinally flexible improves the trackability and pushability of the device through a patient's vasculature, in that the device can more easily curve through tortuous vessels during the introduction procedure.

Figure 5:
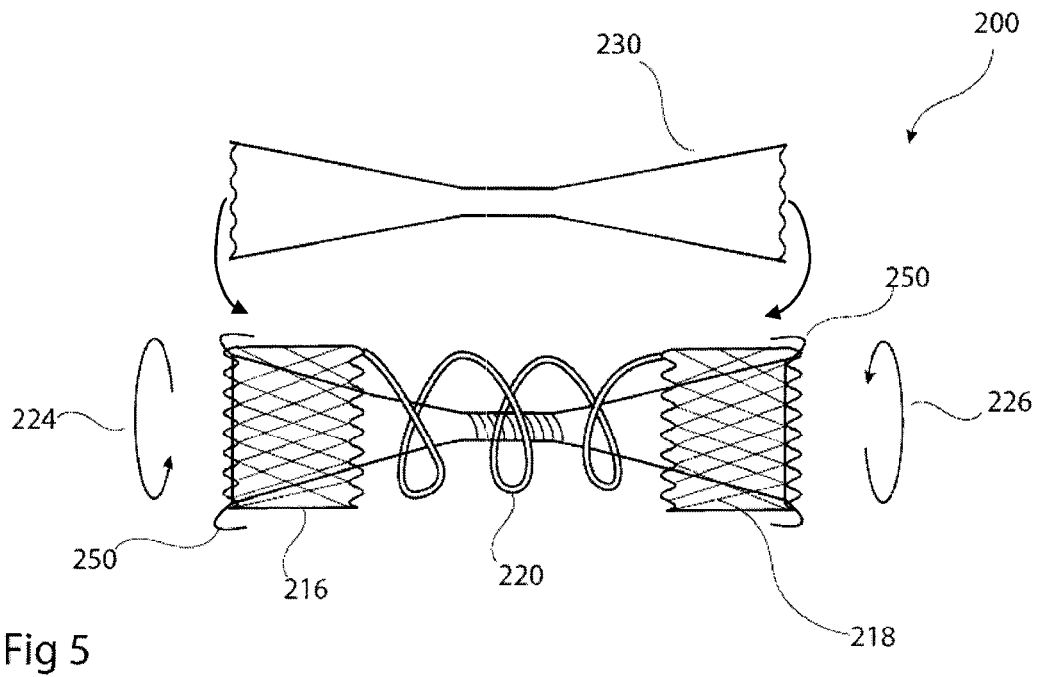
FIG. 5 is a schematic diagram of another embodiment of implantable medical device.
Figure 6:
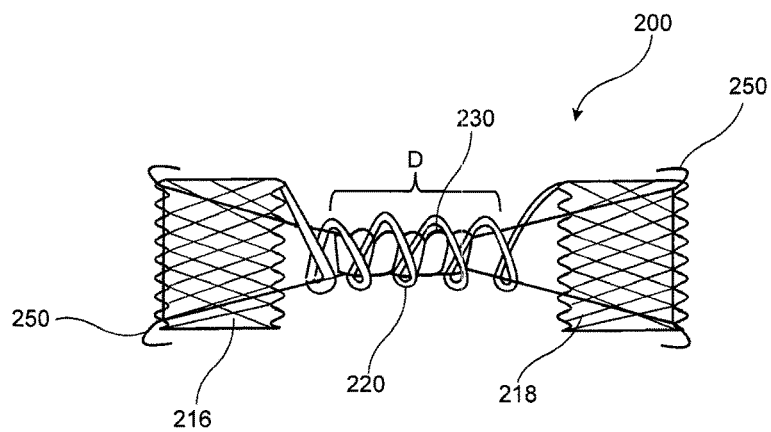
FIG. 6 is a schematic diagram of the device of FIG. 5 in a deployed configuration.

Another embodiment of device is shown in FIGS. 5 and 6, which has similar characteristics to the device of FIGS. 1 to 4 described above.

The implantable medical device 200 includes first and second radially expandable end elements 216, 218 which may be similar to the end elements 16, 18 of the embodiments of FIGS. 1 to 4. The device 200 also includes an intermediate element which in this example is in the form of a wire 220 connected at either end to a respective one of the end elements 216, 218. The wire element 220 preferably extends helically about an intermediate portion of the device 200, as shown in FIG. 5, although it is not excluded in some embodiments that the wire may be substantially straight between the first and second end elements 216, 218. FIGS. 5 and 6 show the device 200 having a single wire 220 but it is to be understood that there may be a plurality of wires 220 connected between the first and second end elements 216, 218, either adjacent one another or radially spaced form one another.

The device 200 also includes a sleeve or tubular element 230 which locates coaxially within the frame structure of the device 200 and has its ends attached to respective ones of the end elements 216, 218, in a similar manner to the tube 30 of the embodiments of FIGS. 1 to 4. In the embodiment shown in FIGS. 6 and 7, the sleeve element 230 could be described as having an hourglass shape, with a waist around its centre point. This is an alternative configuration for the sleeve of the device and in other embodiments the sleeve 230 could be generally cylindrical when untwisted, as in the embodiments of FIGS. 1 to 4. Similarly, the embodiments of FIGS. 1 to 4 could have a sleeve similar to the sleeve 230, that is one with a central constriction or hourglass shape as shown.

The intermediate wire element 220 is wrappable or coilable around the sleeve 230 by relative rotation of the end elements 216, 218, as depicted by the arrows 224, 226 in FIG. 5. When uncoiled or only slightly coiled, the wire 220 will have no turns around the sleeve 230 or only loose turns of a relatively large diameter and the coil 220 will therefore not impinge upon the sleeve 230, which will have an open passage therethrough for receiving a guide wire 62 as explained above. On the other hand, when the end elements 216, 218 are rotated around the longitudinal axis of the device 220, the wire 220 will twist around the sleeve 230 with the turns of the coil becoming increasingly tight so as to constrict the sleeve 230, as shown in FIG. 6. It is preferred that the wire 230 is coiled sufficiently so as to close the lumen or passage through the sleeve 230. That is, it is preferred that the coil turns are so tight that they squash the sleeve 230 into a closed configuration. This can be achieved, as shown in FIGS. 5 and 6, by having a plurality of turns of the coil 220, which also has the advantage of creating a relatively long area of constriction or closure to the sleeve 230, depicted by the distance 0 in FIG. 6. A longer constricted portion can ensure more secure closure of the lumen through the sleeve 230.

In the embodiment of FIGS. 5 and 6 the wire 220 could be made of a spring material, and which can therefore be twisted to a more open configuration as shown in FIG. 6 against spring force. Similarly, the wire 220 can be made of a shape memory material and set to have a memorised shape in the closed configuration of FIG. 6 and openable to tend away from that memorised shape. In the preferred embodiments the wire 220 is made of a plastically deformable material, that is a material not exhibiting significant spring qualities. Examples include: a metal alloy, including Nitinol, a shape memory polymer, steel and so on.

FIGS. 5 and 6 also show the device 200 provided with barbs 250, or other anchoring elements, extending from the first and second end elements 216,218, for securing the end elements 216,218 to the walls of a patient's vessel. Barbs of this nature are well known in the art and it is to be understood that the embodiments of FIGS. 1 to 4 may equally be provided with similar barbs or other anchoring elements. In some embodiments, secure coupling to the vessel wall may be achieved solely by the spring force exhibited by the end elements, without the use of barbs.

Figure 7:
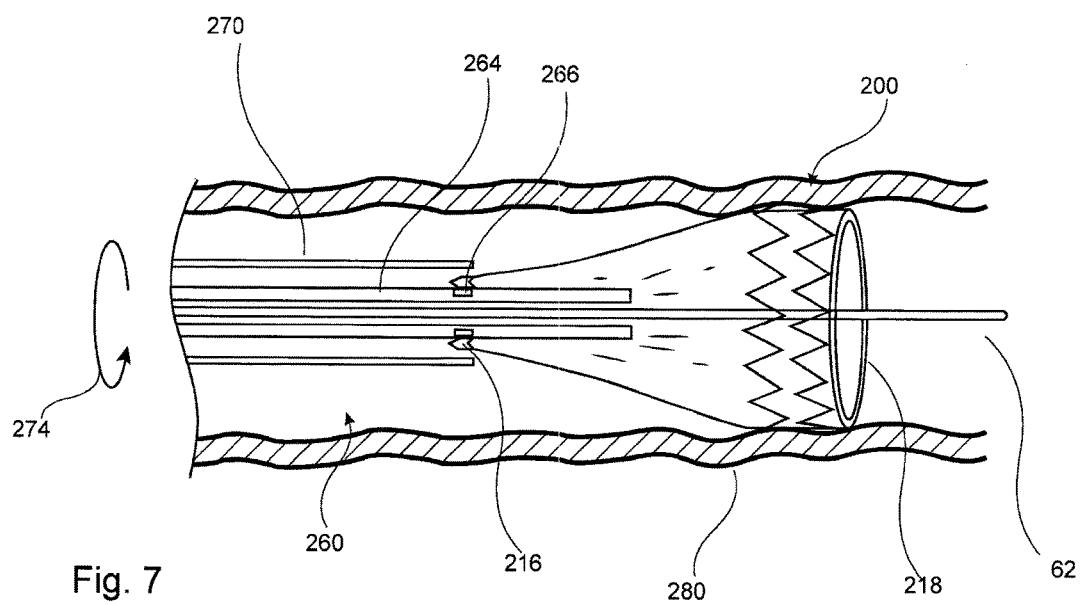
FIG. 7 is a schematic diagram of the distal end of an introducer assembly in the process of deploying the medical device of FIG. 5.

Referring now to FIG. 7, this shows an example of deployment assembly for deploying the device 200 shown in FIGS. 5 and 6. This can be achieved over a guide wire 62 as with the embodiments of FIGS. 1 to 4 and by means of an introducer assembly 260 having some similarities to that shown in FIG. 4, with a carrier catheter 264 for holding the device 200 in a radially constrained configuration, by means of suitable retaining devices 266. As will be seen in FIG. 7, the first, or proximal, end 218 of the device 200 has been deployed, that is radially expanded against the walls of the vessel 280. The other end 216 of the device, which can be termed the distal end of the device, is still retained radially constrained on the carrier catheter 264 and held thereto. Optionally, it will still also be disposed within the sheath 270.

Once the first or proximal end 218 of the device 200 has been deployed in the vessel 280, the introducer assembly 260 can be rotated, as shown by the arrow 274, so as to cause the wire or wires 220 to coil around the sleeve 230 and thereby to constrict the lumen through the sleeve 230. It will be understood that this will be done after removal of the guide wire 62. Once it has been deemed that the wire 220 has been coiled sufficiently, the distal end 216 of the device 200 can be released from the introducer assembly, in particular from the carrier catheter 264, such that the distal end 216 can expand radially outwardly until it comes into abutment with the walls of the vessel 280 and become secured thereto.

The device 200 can therefore provide instant inclusion of the vessel 280 upon its deployment and by a mechanical closure which is secure and with little risk of recanalization of the vessel 280. Furthermore, it is to be appreciated that the wire 220 can be twisted within a range of number of turns yet still create satisfactory closure of the sleeve 230. Furthermore, the wire 200 will constrain the sleeve 230 over a significant length to provide secure closure thereof. In other words, the device will not close only upon a precise number of turns of the distal end 216 relative to the proximal end 218 of the device 200 but over a range thereof, giving a degree of user tolerance.

It will be appreciated also that as the wire 220 is coiled in this manner, the tube 230, by virtue of being attached to the ends 216, 218 of the support structure of the device 200, will twist on itself to close the lumen therethrough, such that the device 200 has a double closure mechanism: the first provided by twisting of the sleeve itself and the second by the tightening of the turns of the coil of the wire 220.

In practice, the sleeve 230 could twist by anything from one turn to a multiple of turns.

In FIGS. 5 and 6 the wire 220 has a length that is greater than the length of the sleeve 230 between the end elements 216 and 218. This is, though, not essential as in other embodiments the wire 220 may be straight and may be of substantially the same length as the sleeve 230. The coiling of the wire 220 will, in such embodiments, result in a shortening of the length of the device 200 as well as twisting of the sleeve 230.

Although the above-described embodiments focus on an occlusion device, the device could similarly be a filter, in which case the sleeve can be made of a filtering mesh, for instance. In other embodiments, the sleeve could be omitted, with the intermediate frame structure of FIGS. 1 and 2 acting as a filter. For this purpose, the skilled person will recognise, the struts of the intermediate structure will have a spacing sufficient to allow the flow of liquid, particularly blood plasma, but small enough to trap debris and thrombus formations.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1411283.3, from which this application claims priority, and in the abstract accompanying this application are incorporated herein by reference.

The invention claimed is:

1. An implantable medical device comprising:
    first and second radially expandable end elements disposed in spaced longitudinal relationship relative to one another, each of the first and second end elements including an interior passage;
    an intermediate element connected between the first and second end elements, the intermediate element providing a passage constriction;
    wherein the intermediate element is formed of a sprung member of twisted unbiased configuration which provides said passage constriction, the sprung member being twistable against spring bias in a direction opposite a direction of twist to open the passage constriction; wherein the device is an occlusion or filter device and includes a tube of occluding or filtering material, the tube including first and second ends attached to respective ones of the first and second end elements and extending across the intermediate element.

2. An implantable medical device according to claim 1, wherein the intermediate element provides a through passage within an interior of the device when twisted against the spring bias.

3. An implantable medical device according to claim 2, wherein the through passage is formed by at least one of expansion and rotation of the tube within the intermediate element.

4. An implantable medical device according to claim 1, wherein the intermediate element closes an interior passage extending through the device.

5. An implantable medical device according to claim 1, wherein the end elements are ring shaped.

6. An implantable medical device according to claim 1, wherein the end elements are each in the form of at least one stent ring.

7. An implantable medical device according to claim 1, wherein the intermediate element is formed from a coil spring.

8. An implantable medical device according to claim 1, wherein at least the intermediate element is formed from spring steel or a shape memory material.

9. An implantable medical device according to claim 1, wherein the end elements and the intermediate element are formed of the same material.

10. An implantable medical device according to claim 1, wherein the end elements and the intermediate element are integral with one another.

* * * * *